(12) United States Patent
Smit

(10) Patent No.: US 7,335,210 B2
(45) Date of Patent: Feb. 26, 2008

(54) ENDOSCOPE AND TOOLS FOR APPLYING SEALANTS AND ADHESIVES AND INTESTINAL LINING FOR REDUCING FOOD ABSORPTION

(76) Inventor: Julie Ann Smit, 1045 Hinman Ave., Evanston, IL (US) 60202

( * ) Notice: Subject to any disclaimer, the term of this patent is extended or adjusted under 35 U.S.C. 154(b) by 943 days.

(21) Appl. No.: 10/115,771

(22) Filed: Apr. 3, 2002

(65) Prior Publication Data
US 2003/0191476 A1 Oct. 9, 2003

(51) Int. Cl.
*A61F 11/00* (2006.01)
(52) U.S. Cl. .................................................. 606/108
(58) Field of Classification Search ............... 606/108; 623/23.64, 23, 23.65; 604/523, 264, 265, 604/500, 28; 424/489
See application file for complete search history.

(56) References Cited

U.S. PATENT DOCUMENTS

| | | | | |
|---|---|---|---|---|
| 4,134,405 | A | * | 1/1979 | Smit ........................ 606/108 |
| 4,315,509 | A | * | 2/1982 | Smit ........................ 606/108 |
| 4,663,308 | A | * | 5/1987 | Saffran et al. ................ 514/3 |
| 5,306,300 | A | * | 4/1994 | Berry ..................... 623/23.64 |
| 6,443,941 | B1 | * | 9/2002 | Slepian et al. ............. 604/522 |

* cited by examiner

Primary Examiner—Anhtuan T. Nguyen
Assistant Examiner—Tuan V. Nguyen

(57) ABSTRACT

A first part of the inventive instrument comprises an insertion and removal device in the form of an endoscope which may be inserted through the mouth, pharynx, esophagus and stomach into the small intestine. The inside lumen of the endoscope contains two extendable tools. One extendable tool has a balloon on its end, which may be inflated and deflated. The other extendable tool contains optical fibers for photopolymerizing adhesives and sealants. The second part of the inventive instrument comprises a tubular lining for implantation in and lining of the small intestine, to prevent food from being absorbed into the villi. The lining is anchored in position by means of medical-grade adhesives that are contained on or applied to a mesh sleeve on one end of the lining. The adhesive-coated sleeve is then expanded and glued to the intestine. In operation the lining expands outwardly as digesting food chemicals enter the lining. This allows the normal bodily peristalsis to squeeze the food chemicals through the lining. An alternate tool for an endoscope may be used to apply a coating of biodegradable sealant to the walls of the small intestine to restrict food absorption. Implanting the lining into the intestine or coating the intestine with sealant can be accomplished without surgery.

15 Claims, 4 Drawing Sheets

ENDOSCOPE AND TOOLS FOR APPLYING SEALANTS AND ADHESIVES AND INTESTINAL LINING FOR REDUCING FOOD ABSORPTION

This invention relates to medical appliances and more particularly to linings and coatings to reduce food absorption in the small intestine, without surgery.

Reduction of food chemicals for weight loss may be accomplished in a number of ways. The inventive instrument aims to accomplish weight loss, without surgery, by implanting a removable lining. The lining is anchored in position by means of medical-grade adhesives that are contained on or applied to a mesh sleeve attached to one end of the lining. The lining covers the intestinal villi and reduces the amount of food chemicals absorbed. When the partially digested food chemicals enter the implant, they are squeezed through the lining by the normal peristaltic movements and contractions, in the patient's body. The lining retains a collapsed state when empty of food and expands outwardly as food chemicals enter. Thus, when the intestinal walls feel a change in diameter, they commence peristaltic movements and contractions, which squeeze the liquefied chyme through the lining and then out its open end.

The lining is inserted and removed, without an operation, by an endoscope, which contains two extendable tools running coaxially within its lumen. One extendable tool has a balloon on its end that may be inflated and deflated. The other extendable tool contains optical fibers to photopolymerize adhesives and sealants once application is complete.

An alternate endoscopic tool may be used to apply a biodegradable medical-grade sealant to coat the intestinal villi to reduce food absorption.

Implanting the intestinal lining and coating the small intestine to restrict food absorption can be accomplished without surgery.

Obesity has become a problem of epidemic proportion in this country. A growing number of people are submitting to surgical treatments wherein portions of the intestine are either cut out, bypassed or stapled to reduce the absorption area of the intestine or interfere with food chemical absorption. Nowadays, the stomach is frequently stapled to reduce the amount of food it will hold. If a person eats too much, the person vomits the excess food from the stomach. The more dangerous operations involving cutting or bypassing the intestine are rather risky and people have even died on occasion.

Thus, there is a need for a less drastic method of reducing caloric absorption, without resorting to surgery.

My two previous U.S. Pat. No. 4,134,405 and No. 4,315,509 were the original prior art in the field of linings, which restrict food absorption in the intestine. The new inventive instrument disclosed, herewith, contains an improved means for anchoring the lining in the intestine. The inventive instrument further discloses other additional improvements and novel alternatives in the field of linings and coatings for the alimentary canal.

Accordingly, an object of the invention is to utilize medical-grade adhesives to glue a lining in the intestine in order to reduce food absorption for the treatment of obesity.

Another object is to coat a portion of the intestinal absorption area with a medical-grade sealant for the treatment of obesity.

Still another object of the invention is to cover an ulcerated portion of the intestine so that it may have time to heal without being exposed to the digestive process, especially the stomach's hydrochloric acid.

A further object is to accomplish these and other objects without permanently altering the alimentary canal.

Yet another object is to accomplish these objects in a manner that may be reversed if unwanted side effects should interfere with normal body processes.

In keeping with an aspect of the invention, these and other objects are accomplished by use of a two-part instrument. The first part of the instrument is an insertion and removal device in the form of an endoscope that may be inserted through the mouth, pharynx, esophagus, and into the stomach or small intestine. The inside of the endoscope contains two extendable tools that run coaxially through its lumen. One extendable tool is equipped with an expandable balloon on its end. The other extendable tool is equipped with optical fibers to photopolymerize adhesives and sealants.

The second part of the instrument is a lining for the intestine. Attached to one end of the lining is a mesh sleeve, which is glued to the walls of the alimentary canal to anchor the lining in position.

Normally, for weight reduction most or all of the lining will be contained in the small intestine. However, the two-part inventive instrument may be utilized anywhere in the alimentary canal it is desired to control, restrict or block absorption.

To insert the lining, the mesh sleeve is coated with primer and adhesives and encased in a gelatin capsule secured over the deflated balloon on the end of the extendable, endoscopic tool. Once the lining and mesh sleeve are correctly positioned, the balloon is inflated, thereby, breaking the gelatin capsule and bonding the mesh sleeve to the intestinal walls.

Thereafter, pulsed ultraviolet light is applied to photopolymerize the adhesive and securely bond it to the intestinal walls. Additional adhesive and light may be applied to the mesh sleeve, if necessary, by an alternate endoscopic tool. After the mesh sleeve is securely glued to the intestinal mucosa, the endoscope is removed from the body leaving the lining anchored in the small intestine.

The lining has a semi-flexible strip, running the length of the lining, which stabilizes the lining and prevents it from twisting shut or kinking.

An alternate endoscopic tool applies a biodegradable sealant to the walls of the small intestine to coat and, thereby, block food absorption into the intestinal villi.

For this procedure, the small intestine is expanded and held open by a Teflon-coated frame, which is extended beyond the endoscope. The Teflon-coated frame is compressed when it is inside the endoscope. The frame expands outwardly, of its own resilience, once it is no longer restricted within the endoscope. A medical-grade sealant is then sprayed or brushed onto the intestinal walls through the frame. A pulsed ultraviolet light is then applied, with the frame still expanding the intestine, to photopolymerize the sealant onto the intestinal walls.

The sealant is biodegradable so it will slowly disintegrate over time and be eliminated by the body.

All tools and instruments contained within the endoscope, which come into contact with the adhesives and sealants, must be coated with Teflon, silicone or other non-stick material so bonding will not occur.

The nature of the preferred embodiments may be understood best from a study of the attached drawings, wherein:

FIG. 1 is a schematic diagram showing the inventive lining being implanted in the small intestine, and the endoscope in a position where it is about to be used to glue the mesh sleeve in position;

FIG. 2 schematically shows, somewhat in perspective, a tubular lining, which may be implanted in the small intestine;

Figures 1, 2:
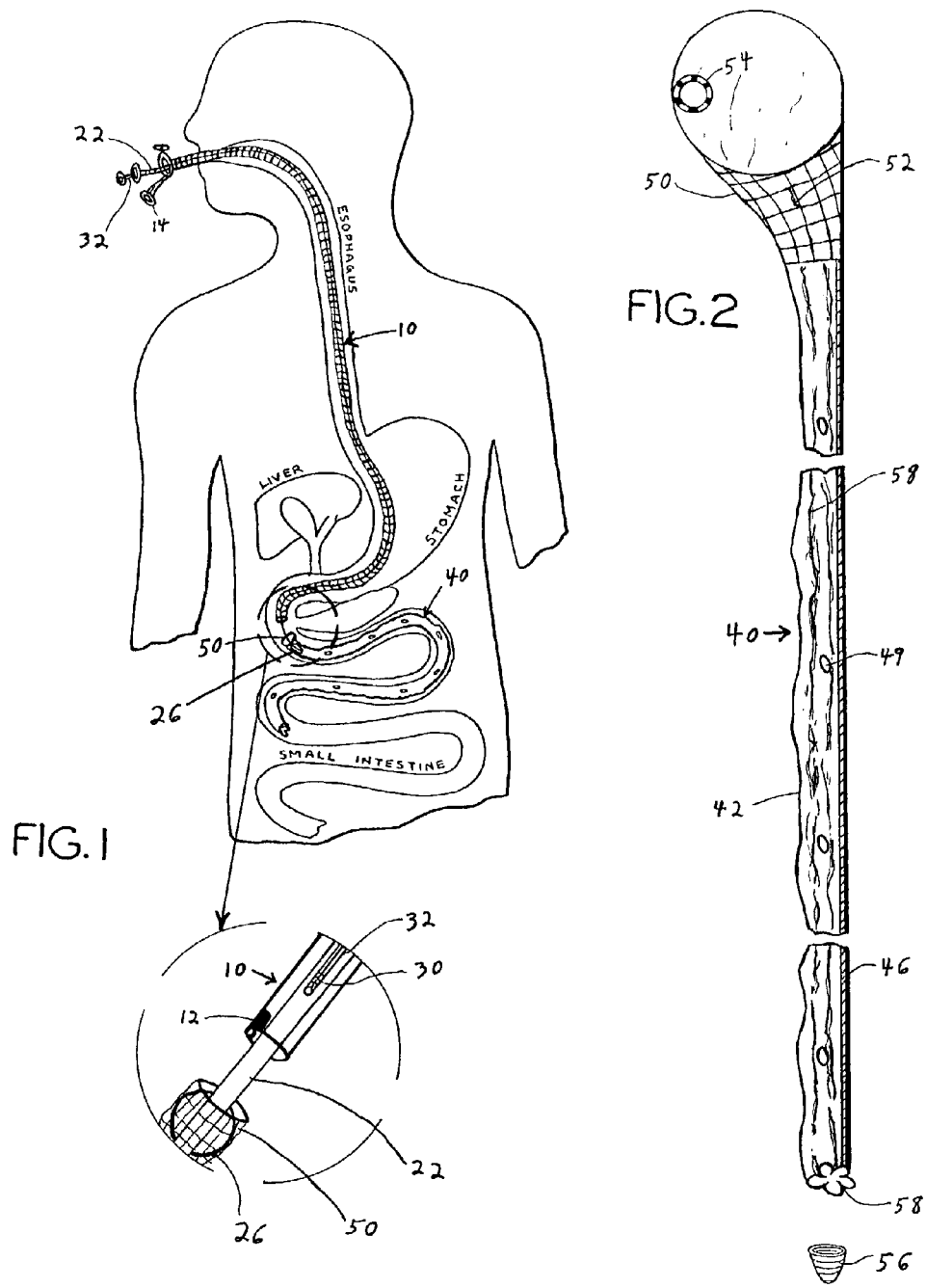

In the description that follows, any suitable medical grade material may be used for the lining, mesh sleeve, endoscope and endoscopic tools. The endoscope and endoscopic tools must be coated with Teflon, silicone or another non-stick material so the adhesives won't bond to them.

The lining is, preferably, manufactured of silicone rubber. The mesh sleeve may be manufactured of any material, which the medical-grade adhesives will securely bond with. In operation, the only portion of the inventive instrument that adhesives are to bond with is the mesh sleeve, which is glued to the walls of the alimentary canal.

Presently the adhesives and sealants of choice include gelatin-based glues which are called hydrogels, marine adhesive proteins, polymeric sealants, fibrin glues, cyanoacrylates, laser solder adhesives, elastromers, collagen-thrombin fleece, bone dust sealants, albumin solutions, and tissue adhesives based on protein engineering.

Several of the above are presently being used instead of sutures and staples for binding of skin and tissues during surgery. The new adhesives and sealants can be engineered to be absorbed, by the body, over a predetermined amount of time.

At present, it is thought that a hydrogel should be used, such as "FocalSeal"."FocalSeal" is a registered trademark for Focal, Inc. And Genzyme Surgical Products' hydrpge; materials and related products. Ethicon, Inc, a Johnson & Johnson Company is marketing the product.

According to the product overview Focal is currently developing two principle FocalSeal Surgical Sealant products for a broad range of applications inside the body. The Company's FocalSeal-L Sealant and FocalSeal-S Sealant are designed to have absorption times that parallel long-term and short-term synthetic, absorbable polymer sutures. Focal believes that these two sealants will be widely applicable to lung surgery, cardiovascular surgery, neurosurgery, gastrointestinal surgery and other surgical applications.

The Company's sealants adhere to tissue as a result of a proprietary 2-step priming and sealing process. The physician first applies a liquid primer that penetrates into the crevices of the tissue, and then the sealant is applied. Both are exposed to a standard wavelength of visible light and in 40 seconds polymerize, or change from a liquid to a solid gel (a process known as photopolymerization). The solid gel formed after the light has been applied is highly flexible, elastic and transparent, and strongly adheres to moist or dry tissue. Focal's products remain adherent during the critical wound healing process, and are then absorbed and eliminated from the body. Regardless of whether "FocalSeal" material is used or not used, the material should have these characteristics.

Additionally, an adhesive hydrogel tape is currently available. Accordingly, the anchoring sleeve could be engineered entirely from hydrogel tape, which would eliminate or reduce the need for primer and adhesive.

A different form of glue utilizes a composition of two-component solutions, which are mixed together at the point of application. They solidify rapidly without a light source. Examples include marine adhesive proteins, collagen-thrombin fleece, fibrin glues, hydrophilic gels, and cyanoacrylates, to name a few.

For tissue welding with adhesives and sealants, the Yag, $CO_2$, THC: Yag and Argon lasers are all being used with success and the laser light could be utilized in the inventive endoscopic tools through the optical fiber.

Currently, many different adhesives and sealants are being successfully utilized during surgery and many more are being experimented with in the field of protein engineering.

These and other suitable materials, adhesives and sealants are used to make the inventive two-part instrument. The first part of the instrument is a maneuverable endoscope 10 (FIG. 1), which is used as an insertion or removal device or tool, which may be inserted through the mouth, pharynx, esophagus, and into the stomach or small intestine. The term "endoscope" has been used throughout this application, however, it should be understood that any form of maneuverable tube or catheter can be employed to contain the insertion and removal tools.

In greater detail, endoscope 10 includes an extendable tool 22, which runs coaxially through the lumen of endoscope 10. The distal portion of extendable tool 22 contains a balloon 26 formed around its outer circumference. Balloon 26 is made of silicone rubber so the adhesive material will not bond to it. Optical fibers 30 are contained within light wand 32 in endoscope 10 for photopolymerizing the adhesives.

The lining 40 (FIG. 2) includes a long and extremely thin-walled tube 42. Thin-walled tube 42 contains a narrow, stabilizing strip 46. Stabilizing strip 46 is semi-flexible to prevent thin-walled tube 42 from twisting shut or kinking as digesting food chemicals are squeezed through it.

Incorporated into one end of thin-walled tube 42 is a mesh sleeve 50. A primer and adhesive coating 52 is applied to mesh sleeve 50 prior to insertion into the body.

Alternately, an anchoring sleeve may be engineered entirely of adhesive hydrogel tape eliminating the need for applying primer and adhesive coating 52.

Figure 3:
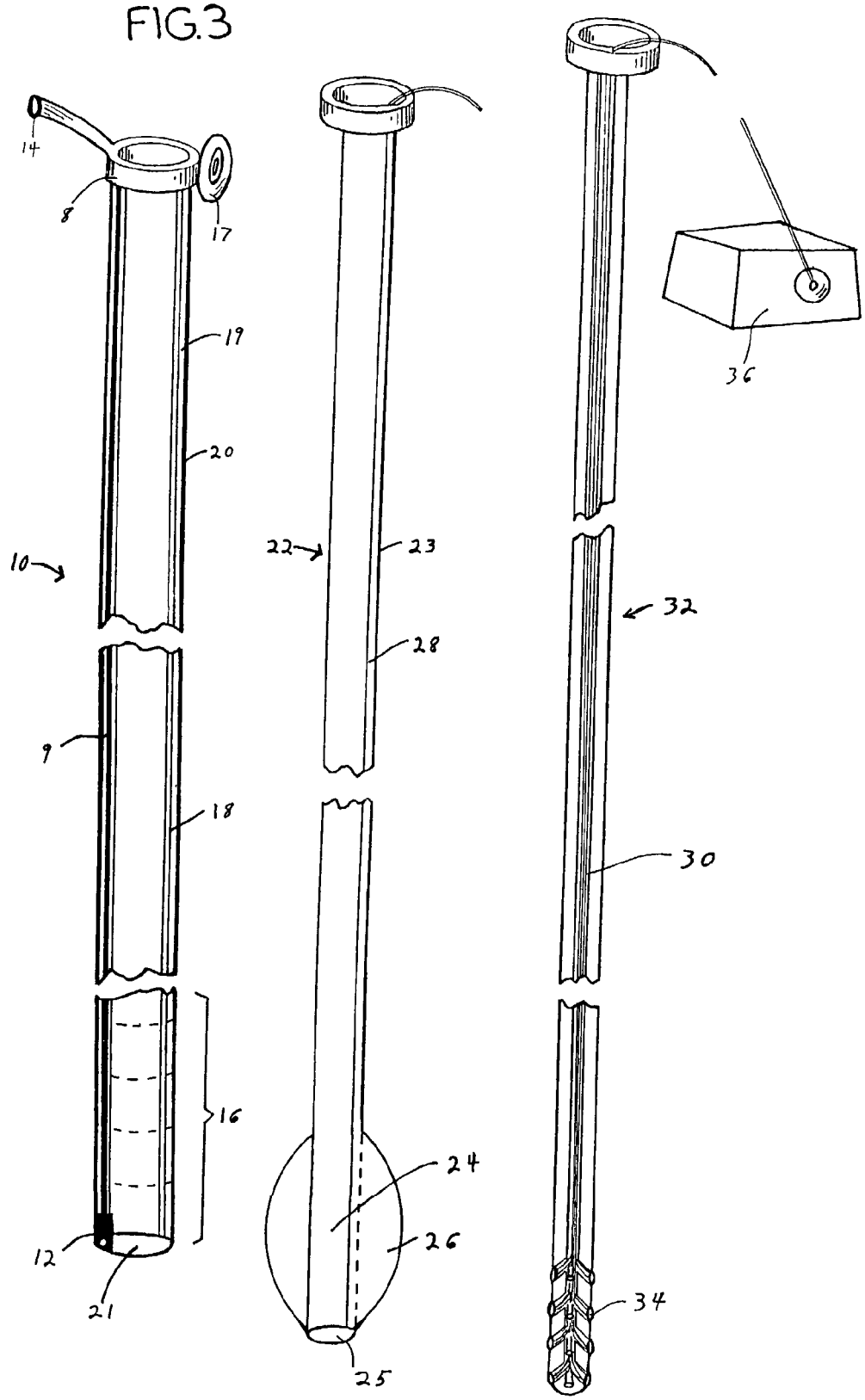
FIG. 3 is a perspective view of the three main parts of the endoscope, which is used as a tool for implanting and removing the lining of FIG. 2.

FIG. 3 shows the endoscope 10 used to insert and remove lining 40. Endoscope 10 is equipped with a camera 12 for viewing inside the body. Optical chamber 9 connects camera 12 and eyepiece 14. The end portion 16 of endoscope 10 is coiled so that it may be maneuvered in a desired direction by adjusting knob 17. Knob 17 controls the angle and direction of end portion 16 via cables 18, which run through tiny passageways 19 within walls 20 of endoscope 10.

The lumen 21 of endoscope 10 contains two extendable tools, which are telescopically fitted together. Extendable tool 22 slides within lumen 21 of endoscope 10 and light wand 32 slides within lumen 25 of extendable tool 22. Both extendable tool 22 and light wand 32 can be extended beyond the distal end of endoscope 10.

Extendable tool 22 has a balloon 26 incorporated around the outer circumference of its end portion 24. An air passageway 28 runs through walls 23 of extendable tool 22. Air passageway 28 is used to inflate and deflate balloon 26.

Light wand 32 contains optical fibers 30 that are connected to a xenon light source 36 located in the procedure room. Photopolymerization occurs after a forty-second pulsed application of light (480-520 nm wavelength), is applied from the xenon light source 36. Ends 34 of optical fibers 30 are directed to point outward to apply the pulsed ultraviolet light to the intestinal walls. Since the ultra violet light is pulsed, the patient is exposed to a minimal amount of ultraviolet light.

For insertion into the body, mesh sleeve 50 is given an application of primer and adhesive coating 52 and then positioned over the deflated balloon 26. The coated mesh sleeve 50, positioned over deflated balloon 26, is encapsulated within a gelatin capsule and pulled inside lumen 21 of endoscope 10.

An alternate method is to manufacture mesh sleeve 50 from adhesive hydrogel tape. For this method, mesh sleeve 50 would be secured over deflated balloon 26, sticky side out, and encased in a gelatin capsule. Mesh sleeve 50 would then be pulled inside lumen 21 of endoscope 10.

Thin-walled tube 42 retains a compressed state from a series of lengthwise folds 58 so further compression is not necessary. However, a gelatin capsule 56 may be placed on the end of thin-walled tube 42 to better streamline it into the body.

Once the physician has determined lining 40 has reached the correct location for implantation, mesh sleeve 50 is released from inside lumen 21. Balloon 26 is then inflated which breaks the gelatin capsule and presses mesh sleeve 50 against the walls of the intestine, thereby, gluing it in place. The physician then deflates and retracts balloon 26 back inside endoscope 10. Light wand 32 is then extended to position ends 34 of optical fibers 30 inside mesh sleeve 50. Opical fibers 30 are energized for forty seconds, via xenon light source 36, to photopolymerize the adhesive and bond mesh sleeve 50 to the intestinal walls. The light wand 32 is then retracted back inside lumen 25. Endoscope 10 is then removed from the body leaving lining 40 anchored in the intestine.

To remove the lining from the body, a slender forceps may be placed inside lumen 21 of endoscope 10 to grasp a loop 54 on mesh sleeve 50. The loop 54 and mesh sleeve 50 are then pulled partially inside endoscope 10 for compression prior to removal from the body.

Balloon 26 and optical fibers 30 could be incorporated into one endoscopic tool instead of two.

Holes 49 may be punched through lining 40 to allow limited food absorption.

Figure 4:
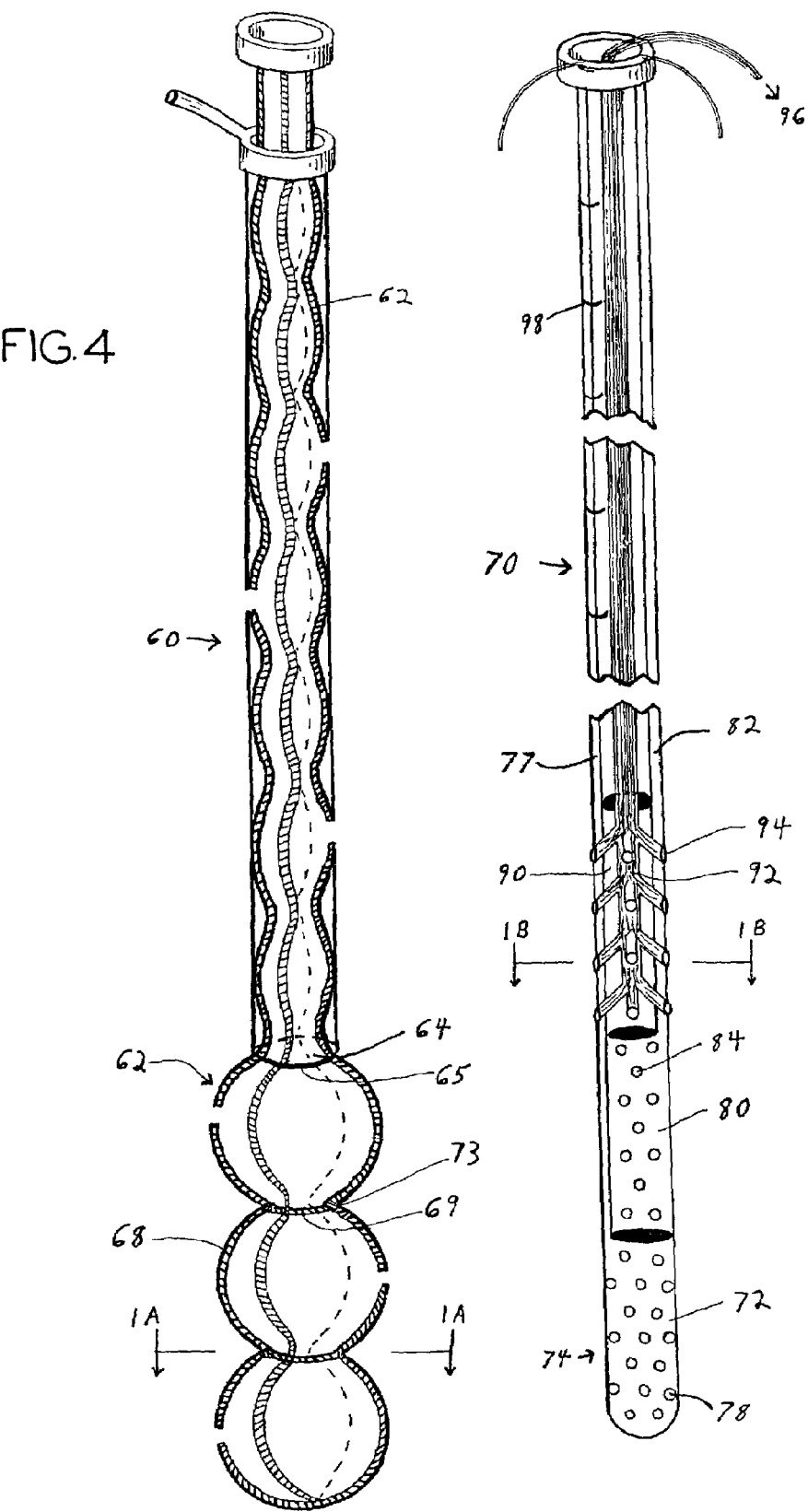
FIG. 4 is a perspective view of the main parts of an alternate endoscope, which shows a frame being extended to expand the intestine and an endocopic tool for spraying and photopolymerizing adhesives and sealants.

FIG. 4 shows an alternate endoscope 60 which can be used to apply adhesives and sealants to the walls of the alimentary canal or additional adhesive to mesh sleeve 50.

In greater detail, endoscope 60 contains a frame 62 which can be extended out from lumen 64 of endoscope 60. Frame 62 is coated with Teflon or other non-stick material to prevent bonding with the adhesives and sealants.

Frame 62 comprises a series of billowed bands 68, which expand outwardly of their own resilience once frame 62 is extended beyond the confines of endoscope 60. Sealant tool 70 slides within the center of frame 62 through rings 69. Rings 69 reinforce and join billowed bands 68 together at constrictions 73.

Figure 5:
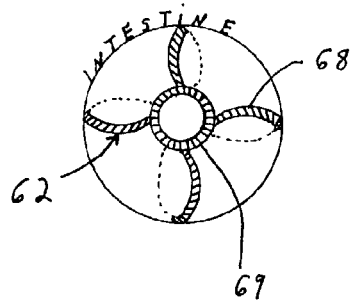
FIG. 5 is a cross section taken along line 1A-1A of FIG. 4 showing the Teflon-coated frame dilating the intestine.

FIG. 5 is a cross sectional view of frame 62 dilating the intestine. Frame 62 dilates the intestine while a biodegradable sealant is sprayed on the intestinal villi. Frame 62 is left in position during the photopolymerization process as it keeps the wet, sealant-coated, intestinal walls away from the optical fiber chamber.

In operation, roughly a two-foot section of the small intestine will be coated with sealant. In a living person the small intestine is approximately five feet in length. The twenty-foot quotes often attributed to the intestinal length are measured in a dead person whose intestine has lost its tonus and with the intestine stretched out to the maximum. Applying sealant to a two-foot portion of the small intestine will result in safe yet reliable weight loss.

In greater detail, sealant tool 70 contains a primer chamber 72 in its distal portion 74. Primer chamber 72 is preferably at least six inches in length to allow at least six inches of the intestine to be primed at one time. A passageway 77, for delivering primer, runs through sealant tool 70. The primer is directed, under pressure, into primer chamber 72 and is sprayed out openings 78.

Directly behind primer chamber 72 is adhesive chamber 80. Adhesive chamber 80 is preferably at least six inches in length to allow at least six inches of the intestine to be coated with adhesive at one time. A passageway 82, for delivering the adhesive, runs through sealant tool 70. The adhesive is directed, under pressure, into adhesive chamber 80 and is sprayed out openings 84.

Behind adhesive chamber 80 is light chamber 90 containing optical fibers 92. Ends 94 of optical fibers 92 are arranged to shine outward so light is directed at the intestinal mucosa. Ends 94 of optical fibers 92 can be circularly arranged to photopolymerize at least six inches of the intestine at one time. Optical fibers 92 are attached to a xenon light source 96 located in the procedure room.

Figure 6:
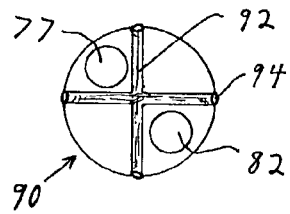
FIG. 6 is a cross section taken along line 1B-1B of FIG. 4 showing optical fibers directed outward to photopolymerize the sealant and bond it to the intestinal walls.

FIG. 6 is a cross section view of light chamber 90 with optical fibers 92 directed outward to photopolymerize the sealant and bond it to the intestinal walls.

Light chamber 90 may be separated several inches or more from the spray chambers to prevent any sealant from splattering on light chamber 90 during the spray process.

Alternately sealant tool 70 may be designed with primer chamber 72 and adhesive chamber 80 constructed around an open lumen. Containing light wand 32 within a lumen running through sealant tool 70 would protect the light chamber even further during the spray operation, if necessary or desired.

In operation, endoscope 60 is inserted through the mouth, pharynx, esophagus, and stomach into the small intestine. Once endoscope 60 is in the desired location, frame 62 is extended approximately two feet beyond the distal end 65 of endoscope 60. Billowed bands 68 in frame 62 expand outwardly which dilates a two-foot portion of the small intestine.

The physician extends sealant tool 70 six inches beyond distal end 65 of endoscope 60. The physician then energizes an outside pump which forces the primer into chamber 72 causing it to be sprayed out openings 78. The doctor sprays this section of the intestine with primer for the necessary amount of time.

The physician then advances sealant tool 70 another six inches to position adhesive chamber 80 in the area just sprayed with primer. The physician energizes an outside pump, which forces the adhesive into adhesive chamber 80 and out openings 84. The doctor sprays the adhesive on top of the primer to thoroughly coat it.

At this point the physician can activate the xenon light source 96 and advance sealant tool 70 to bring light chamber 90 into the area just sprayed with primer and adhesive. Light chamber 90 photopolymerizes the sealant in 40 seconds. This turns the sealant into an elastic gel-like substance, which bonds to and coats the intestinal walls. Frame 62 holds the wet, sealant-coated, intestinal mucosa away from light chamber 90 during the photopolymerization process.

The doctor can alternately coat the remaining portion of the expanded intestine with primer, adhesive and light by advancing sealant tube 70.

Sealant tool 70 may be marked in inches 98 to aid the doctor in how far to advance the tube.

Additionally, sealant tool 70 may be exchanged with other endoscopic tools. For example, sealant tool 70 may be inserted into endoscope 10 (FIG. 3), to apply more primer and adhesive to and through mesh sleeve 50.

Also, laser light could be brought through optical fibers 92 when sealant bonding using laser light is desired. For this a low-power laser must be used.

Figure 7:
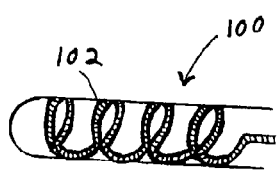
FIG. 7 shows a heat coil which may be used to bond adhesives and sealants.

FIG. 7 shows a chamber 100, which utilizes temperate heat to bond adhesives and sealants to the intestinal walls. A heat coil 102 is properly insulated and incorporated into one of the endoscopic tools in lieu of the light chamber.

Figure 8:
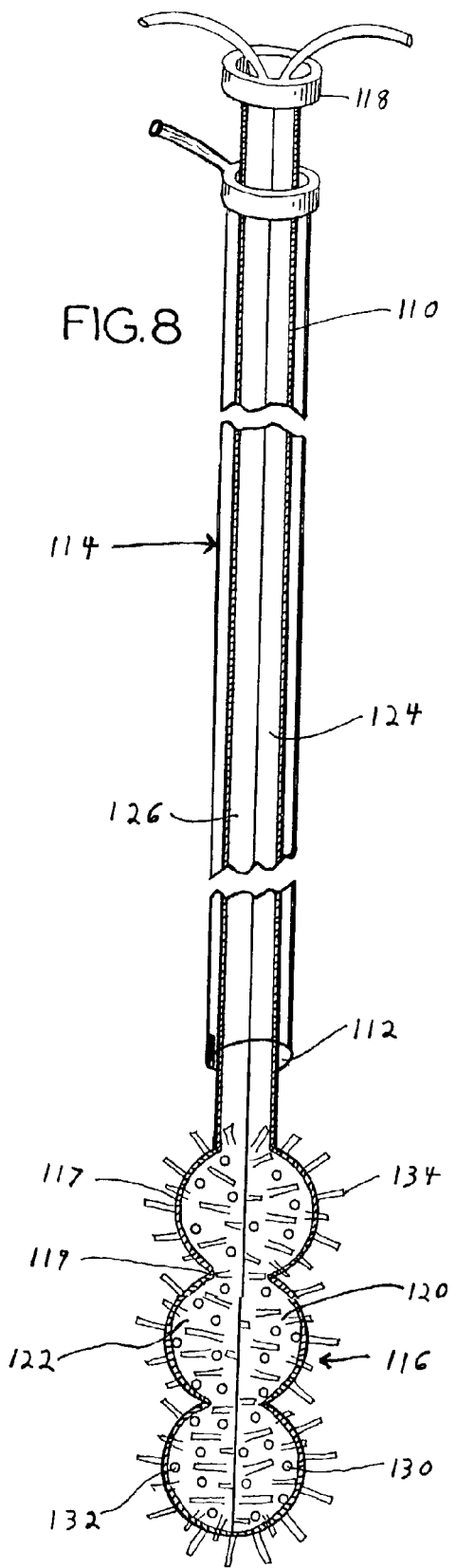
FIG. 8 is a perspective view of an alternate endoscope, which contains a brush that can be rotated, to apply and mix two-component adhesives and sealants.

FIG. 8 shows an applicator 110 for applying adhesives and sealants. Applicator 110 is used in conjunction with two-compound sealants that must remain separated until application, because they solidify rapidly after contact with each other. Normally, a light source is not necessary to solidify these two-component sealants.

In greater detail, applicator 110 fits within lumen 112 of endoscope 114. The applicator 110 contains a brush portion 116 and a handle portion 118. The brush portion 116 has a series of billows 117 and constrictions 119 to better coat the uneven intestinal mucosa.

Brush portion 116 is preferably at least six inches in length to coat at least six inches of the alimentary canal at a time. Applicator 110 is coated with Teflon, silicone or other suitable non-stick material.

Brush portion 116 contains two bladders 120 and 122, which are of a semi-crushable nature. When brush portion 116 is pulled inside endoscope 114, the billows 117 compress. When brush portion 116 is released from the confines of endoscope 114, the billows 117 expand of their own resilience and dilate the intestinal walls. This slight pressure on the intestine produces a tighter bond between the sealant and the intestinal mucosa. The slight pressure, also, allows bristles 134 to better mix and blend the two-compound sealant.

Sealant is delivered to bladder 120 through tube 124 and a different sealant compound is delivered to bladder 122 through tube 126. A multiplicity of openings 130 are formed through bladder 120. Bladder 122, also, contains a multiplicity of openings 132.

Bristles 134 of various lengths are formed over the surface of brush portion 116. Bristles 134 are of a soft nature and of different lengths to better mix the two-compound sealant into the rough intestinal mucosa.

In operation, a physician extends brush section 116 six inches beyond the end of endoscope 114. The physician then energizes an outside pump, which forces the two separate sealants, into bladders 120 and 122. The sealants then flow out openings 130 and 132. At this point the physician disconnects the sealant tubes and rotates handle 118 for approximately one minute so the bristles 134 mix and blend the two sealants together. Endoscope 114 acts as a sheath and protects the body from irritation while applicator 110 is being turned. Within five minutes the combined sealants form a solidified, gel-type coating over the intestine.

Applicator 110 should not be extended to coat the next section of intestine until the sealant has had a chance to solidify. Brush section 116 being a non-stick material can dilate the intestine, during the polymerization process, without adhesion occurring.

A Teflon-coated frame can, also, be utilized in conjunction with endoscope 114 to dilate the intestine during the sealant application and polymerization process.

There are other applications for lining or coating portions of the alimentary canal. For example, duodenal ulcers, which are the most common, are aggravated by the stomach's hydrochloric acid constantly emptying onto the ulcer, thereby, eroding it further. A lining or coating over the ulcer would prevent hydrochloric acid from coming into contact with the ulcer and allow it to heal.

To treat duodenal ulcers, the lining would commence in the stomach and bypass the hydrochloric acid through the lining instead of onto the ulcer.

Diverticular disease could, additionally, be treated with the lining. Diverticulosis is the presence of small, saclike swellings in the walls of the alimentary canal. When the sacs become infected with stagnant food, it is a medical emergency usually requiring surgery. The lining could be glued over each diverticula after the pouch is flushed with water. The lining would prevent digesting food chemicals from becoming trapped in the diverticula.

In operation, different components of the endoscopic tools could be interchanged with each other. Also, large portions of the lining could be made of adhesive hydrogel tape or the entire lining could be made of mesh and glued into position. For these applications, balloon 26 could be any length necessary in order to press and bond the mesh or hydrogel lining onto the walls of the alimentary canal.

Additionally, the lining and/or endoscope could be inserted through the rectum, which would allow a physician to use an endoscope with a wider inside lumen for containing the tools. For this application the various chambers could be in the reverse order.

Also, the tip of an endoscope, maneuverable catheter or endoscopic tool could contain an ultrasound transducer to aid in insertion and removal of the lining or aid in coating of the intestine.

Also, a series of tiny mirrors could be utilized with the optical fibers to aid in the photopolymerization process.

Those skilled in the art will readily perceive still other changes and modifications which may be made in the inventive structures and perceive new and different uses for the inventive structures. Therefore, the appended claims are to be construed broadly enough to cover all equivalent structures falling within the scope and the spirit of this invention.

I claim:

1. An instrument for use in applying a coating to an interior surface of an intestine for restricting food absorption, the instrument comprising:
 a flexible endoscopic member having a proximal end, a distal end, wherein the distal end configured to be inserted into the intestine, and a lumen therethrough;
 a second elongate member to be inserted through the lumen of the flexible endoscopic member, wherein the second elongate member having a proximal portion, a distal portion, a passageway, and a plurality of flexible bands disposed at least on the distal portion, said the flexible bands configured to expand outwardly to contact the interior surface of the intestine and radially expand the intestine when the distal portion of the second member extended beyond the distal end of the first member;

a coating delivery tool configured to be inserted into the passageway of the second member, said coating delivery tool having a proximal portion, a distal portion configured to extend beyond the distal portion of the flexible endoscopic member for applying a coating to the interior surface of the intestine, at least one internal passage, and an outer surface, said the proximal portion further includes a first chamber at a distal end of the distal portion for storing a first component of an adhesive or sealant, wherein the first component configured to coat the interior surface of the intestine, a second chamber located proximal to the first chamber for storing a second component, wherein the second component of an adhesive or sealant configured to coat the interior surface of the intestine.

2. The instrument of claim 1, wherein the first component is a biodegradable primer.

3. The instrument of claim 1, wherein the second component is a biodegradable adhesive or biodegradable sealant that is configured to be slowly disintegrated over time and eliminated by the body.

4. The instrument of claim 3, wherein the second component is a photopolymerizing biodegradable sealant or photopolymerizing biodegradable adhesive.

5. The instrument of claim 4, wherein the coating delivery tool further comprises plurality of side openings on the outer surface wherein the plurality of side opening configured to receive optical fibers, wherein the optical fibers operative coupled to a laser, configured for curing the sealant after the sealant being applied to the interior surface of the intestine.

6. The instrument of claim 3, wherein the coating delivery tool further comprises a heating coil, wherein the heating coil operative coupled to a heat source, configured for curing the adhesive or sealant after the adhesive or sealant being applied to the interior surface of the intestine.

7. The instrument of claim 1, wherein the second elongate member further comprises a coating that prevent adhesive and sealant bonding to the second member.

8. The instrument of claim 1, wherein the flexible endoscopic member further includes an ultrasound transducer, said the ultrasound transducer configured to aid a surgeon to accurately positioning the distal end of the endoscopic member inside the intestine.

9. The instrument of claim 1, wherein the second elongate member further includes markings on the outer surface, said the markings configured to aid a surgeon to accurately positioning the distal end of the second member inside the intestine.

10. A method for applying a coating to an interior surface of an intestine for partially restricting food absorption from the inside of the intestine to the body thereby treating obesity, the method comprising:
  providing an instrument as in claim 1,
  inserting the distal end of the flexible endoscopic member into the intestine,
  inserting the second elongate member into the lumen of the flexible endoscopic member,
  extending the distal portion of the second elongate member beyond the distal end of the endoscopic member thereby expanding the distal portion of the second elongate member outwardly to contact the interior surface of the intestine and radially expand the intestine,
  inserting the coating delivery tool into the passageway of the second member and positioning the distal portion of the coating delivery tool proximate to the distal portion of the second member,
  applying the first component of an adhesive or sealant to the interior surface of the intestine,
  applying the second component of an adhesive or sealant to the interior surface of the intestine, and
  applying energy to cure the coating.

11. A method of claim 10, wherein the first component is a biodegradable primer.

12. A method of claim 10, wherein the second component is a biodegradable adhesive or biodegradable sealant that is configured to be slowly disintegrated over time and eliminated by the body.

13. A method of claim 12, wherein the energy being applied is heat.

14. A method of claim 12, wherein the energy being applied is laser.

15. A method of claim 12, wherein the biodegradable adhesive or biodegradable sealant is a photopolymerizing biodegradable adhesive or photopolymerizing biodegradable sealant, respectively.

* * * * *